United States Patent [19]

Friedrich et al.

[11] Patent Number: 5,523,287
[45] Date of Patent: Jun. 4, 1996

[54] THROMBIN-INHIBITORY PROTEIN FROM ASSASSIN BUGS

[75] Inventors: Thomas Friedrich, Darmstadt; Siegfried Bialojan, Oftersheim; Burkhard Kroeger, Limburgerhof; Christoph Kuenast, Otterstadt, all of Germany

[73] Assignee: BASF Aktiengesellschaft, Ludwigshafen, Germany

[21] Appl. No.: 211,942

[22] PCT Filed: Oct. 27, 1992

[86] PCT No.: PCT/EP92/02450

§ 371 Date: Apr. 26, 1994

§ 102(e) Date: Apr. 26, 1994

[87] PCT Pub. No.: WO93/09232

PCT Pub. Date: May 13, 1993

[30] Foreign Application Priority Data

Nov. 6, 1991 [DE] Germany .......................... 41 36 513.5

[51] Int. Cl.$^6$ .......................... C07K 14/81; A61K 38/57; C12N 15/15

[52] U.S. Cl. .......................... 514/12; 530/350; 530/856; 514/822; 536/23.5

[58] Field of Search .......................... 530/350, 856; 536/23.5; 514/12, 822

[56] References Cited

U.S. PATENT DOCUMENTS 5,093,322  3/1992  Bonin et al. .......................... 514/21

FOREIGN PATENT DOCUMENTS 2054190  3/1991  Canada .
345614  12/1989  European Pat. Off. .
3931739  4/1991  Germany .
1092421  11/1967  United Kingdom .

*Primary Examiner*—Charles L. Patterson, Jr.
*Assistant Examiner*—Rebecca Prouty
*Attorney, Agent, or Firm*—Keil & Weinkauf

[57] ABSTRACT

A novel thrombin-inhibitory protein from assassin bugs with a molecular weight of about 12,000 dalton and the N terminus Glu-Gly-Gly-Glu-Pro-Cys-Ala-Cys-Pro-His-Ala-Leu-His-Arg-Val-Cys-Gly-Ser-Asp is described. The protein is suitable for controlling diseases.

5 Claims, No Drawings

THROMBIN-INHIBITORY PROTEIN FROM ASSASSIN BUGS

The present invention relates to a novel thrombin-inhibitory protein from assassin bugs and to a process for preparing it.

Thrombin inhibitors are important therapeutic substances used, for example, for the prophylaxis or treatment of thromboses or arterial reocclusions.

German Offenlegungsschrift DE 39 31 839 describes a thrombin inhibitor which has been isolated from the argasid tick Ornithodoros moubata. This protein has a molecular weight of about 15,000 dalton, an isoelectric point at pH 4–5 and the N-terminal amino-acid sequence SDYEFPPP-KKXRPG.

European Published Application EP 345 614 describes the thrombin inhibitor amblyommin which is isolated from bont ticks. This is a protein with a molecular weight of 20,000–30,000 dalton and an isoelectric point at pH 5.05–5.65.

However, to date no protein with thrombin-inhibitory action has yet been found to be suitable and advantageous as a drug in terms of high activity, lack of antigenicity, long biological half-life, and few side effects such as risk of hemorrhage.

It is an object of the present invention to provide novel thrombin inhibitors which are suitable as drugs in terms of the abovementioned properties.

We have found that this object is achieved by a novel thrombin-inhibitory protein isolated from assassin bugs.

The novel protein has the following physicochemical properties. Molecular sieve chromatography shows that it has a molecular weight of 20,000–24,000 dalton. A molecular weight of 12,000±2000 dalton is determined in an SDS polyacrylamide gel. The determination of the isoelectric point shows that it is at pH 3.7–4.7.

The protein binds specifically to a thrombin affinity column. It inhibits the biological activity of thrombin in an in vitro enzyme assay.

The following N-terminal amino-acid sequence was determined for the protein (SEQ ID NO: 1): Glu-Gly-Gly-Glu-Pro-Cys-Ala-Cys-Pro-His-Ala-Leu-His-Arg-Val-Cys-Gly-Ser-Asp The protein according to the invention contains a sequence of 103 amino acids which is shown in sequence listing SEQ ID NO: 3.

The DNA coding for this sequence of 103 amino acids is likewise detailed in sequence listing SEQ ID NO: 2.

The protein according to the invention may additionally contain further amino acids at the C terminus. It is likewise possible for the protein to contain at the N terminus other amino-acid sequences such as natural or heterologous leader sequences or additional amino acids such as methionine.

It is possible to predict from the amino-acid sequence indicated in sequence listing SEQ ID NO: 3 that there are two domains in this molecule. The first domain is limited essentially by the cysteine residues at positions 6 and 48, and the second domain by the cysteine residues at positions 57 and 101.

The invention also relates to DNA sequences which code for proteins having a thrombin-inhibitory action and which are selected from the group formed by a) DNA sequences with the structure described in SEQ ID NO: 2, SEQ ID NO: 4, SEQ ID NO: 6, SEQ ID NO: 8, SEQ ID NO: 10, SEQ ID NO: 12 and SEQ ID NO: 14, and b) DNA sequences which hybridize under standard conditions with DNA sequences a).

These DNA sequences are for thrombin inhibitors having up to 6 domains.

The invention also relates to smaller proteins which contain only one of these two domains. Proteins according to the invention also include those which contain a plurality, preferably up to 10, of such domains.

In this connection, the minimum requirements for a single active domain are the amino acids (from SEQ ID NO: 7) from position 6 to 48, 57 to 101 or 119 to 160 or the amino acids from SEQ ID NO: 17 from position 6 to 48, 57 to 101, 120 to 161, 190 to 232, 241 to 285 or 303 to 344.

N-Terminal and C-terminal extensions do not interfere with the thrombin-inhibiting activity. Extensions of these types may contain sequences such as, for example, the amino acids 1 to 5, 49 to 56, 102 to 118, 161 to 170 from SEQ ID NO: 7 or 1 to 5, 49 to 56, 102 to 119, 162 to 189, 233 to 240, 286 to 302 or 345 to 354 from SEQ ID NO: 17.

These amino-acid sequences, which are distinguished by high flexibility and hydrophilicity, can be employed as spacers between the individual domains. Multidomain proteins of these types have a prolonged half-life without any essential reduction in the activity of the individual domains.

Owing to the insensitivity of the novel protein and its individual domains to extensions at the N terminus and C terminus, heterologous linkage of the novel thrombin inhibitor with other proteins is also possible. Examples of such proteins are tissue plasminogen activators, streptokinase, urokinase, antithrombin III and activated protein C. A protein which is important for lysis therapy is tPA, its muteins and derivatives. The advantage of such fusion proteins is an increased thrombous specificity with, at the same time, a reduction in the reocclusion rate.

For example, the amino-acid sequence of tissue plasminogen activator (EP 93619) at position 1-527 is extended with amino acids 1–104 of the double-headed thrombin inhibitor by attaching via suitable restriction sites the corresponding nucleotide sequence from (SEQ ID NO: 2 downstream of the nucleotide sequence coding for tPA 1-157.

Conversely, however, it is also possible, for example, to extend the nucleotide sequence from amino acid 104 of the double-headed inhibitor with the sequence for tissue plasminogen activator by amino acid 1 of tPA becoming amino acid 105 of the heterotrimeric protein.

Such combination proteins result in a higher clot specificity because the thrombin inhibitor selectively binds to the thrombin entrapped in the thrombus and thus brings its fusion partner up to the clot.

An alternative strategy is to provide the fusion protein described above with a sequence which can be cleaved by proteases (e.g. a factor Xa cleavage site (ILE-GLU-GLY-ARG-X)) which results, after activation of the coagulation system, in liberation of the fusion partners in order to exert, for example, their fibrinolytic and anticoagulant effect. It is possible for a plurality, preferably from 2 to 10, fusion partners to be put together in this way.

Such proteins which contain a plurality of these domains are expediently prepared by genetic manipulation. For example, the DNA sequences which code for the domains are linked by conventional methods to give a synthetic multidomain gene, and this gene is expressed in a conventional manner.

The novel protein can be isolated from assassin bugs of the genus Rhodnius. To do this, the bugs are homogenized, expediently in a buffer at pH 6–9, preferably pH 7–8, with a homogenizer, preferably a mixer. The insoluble constituents are then removed, preferably by centrifugation.

The protein can be further purified by chromatographic methods, preferably ion exchange chromatography and/or affinity chromatography. A purification step by thrombin affinity chromatography is particularly preferred.

The purification of the protein can be monitored by a thrombin activity assay. It is expedient to use an optical assay in which a chromogenic substrate, for example Chromozym T, is converted by thrombin. The fractions containing the novel protein can be identified by their thrombin-inhibiting action on addition to this optical assay.

Genetic engineering methods are particularly suitable for preparing the protein according to the invention.

To do this, a cDNA gene bank from the assassin bug is constructed in a conventional manner. It is possible to isolate the gene coding for the protein according to the invention from this gene bank by, for example, preparing a DNA probe whose sequence is obtained from the N-terminal amino-acid sequence described above by translation back using the genetic code. The appropriate gene can be found and isolated by hybridization with this DNA probe.

However, it is also possible to employ the polymerase chain reaction (PCR) technique to prepare the appropriate gene. For example, a primer whose sequence has been obtained by translation back from the N-terminal amino-acid sequence described above, and a second primer whose sequence is complementary to the 3' end of the cDNA gene fragment, preferably with the sequence poly(dT), can be used to prepare the cDNA gene fragment for the protein according to the invention by the PCR technique. The appropriate gene can also be isolated by constructing an expression gene bank from assassin bugs and screening this with an antibody directed against the protein according to the invention.

Once the appropriate gene has been isolated, it can be expressed by genetic engineering methods in organisms, e.g. in bacteria, yeasts, eukaryotic cells, with the aid of an expression vector in a conventional manner.

It is preferable to use prokaryotes such as *E. coli*, and strongly expressing vectors, e.g. under the control of the inducible tac promoter as is present, for example, in the plasmid pMal-p2 (Protein Fusion and Purification System, "GeneExpress", New England Biolabs). This results in periplasmic expression of a fusion protein composed of the maltose binding protein and the thrombin inhibitor described. The fusion partner can be removed enzymatically after purification.

The general procedure for the preparation by genetic engineering of a novel protein when the partial amino-acid sequence is known is described in textbooks of genetic engineering, for example E. L. Winnacker, Gene und Klone, Verlag Chemie, Weinheim, 1984. The experimental conditions for the individual methods, such as construction of a gene bank, hybridization and expression of a gene, are described in T. Maniatis, Molecular Cloning, Cold Spring Harbor Laboratory, 1990.

Standard conditions mean, for example, temperatures from 42° to 58° C. as an aqueous buffer solution with a concentration of from 0.1 to 1×SSC (1×SSC: 0.15M NaCl, 15 nM sodium citrate pH 7.2).

The protein according to the invention is preferably used in the form of its pharmaceutically acceptable salts.

The novel protein has anticoagulant properties. It can be used, for example, for the prophylaxis of thromboses or arterial reocclusions, for the treatment of thromboses, for conserving blood or in extracorporeal circulations.

The novel proteins are effective thrombin inhibitors. They can be used as drugs alone or together with known anticoagulant factors. The anticoagulant factors which are preferably employed are thrombin inhibitors, for example hirudin, factor Xa inhibitors, for example TAP (Waxman et al., Science 248 (1990) 593–596) or platelet aggregation inhibitors, for example kistrin (Dennis et al., Proc. Natl. Acad. Sci. USA 87 (1989) 2471–2475).

The invention is further illustrated by the following examples.

EXAMPLE 1

Purification of the thrombin-inhibitory protein from assassin bugs

A laboratory culture of the bugs (Rhodnius prolixus) was maintained at 28° C. and 80% relative humidity. The bugs were allowed to feed off rabbits at 30-day intervals. After the bugs had reached the last stage of development they were frozen at −20° C.

25 g of bugs were homogenized with 75 ml of 20 mM sodium phosphate buffer, 150 mM NaCl (pH 7.5). The homogenate was centrifuged at 20,000 rpm (Sorvall RC-3B, rotor SS-34) for 60 minutes. The precipitate was discarded.

The protein solution (supernatant) was loaded (60 ml/h) onto a Q-Sepharose® column (Pharmacia) which had been equilibrated in 20 mM sodium phosphate buffer pH 8.0 (diameter 2.5 cm, volume 50 ml).

The column was washed with 10 column volumes of equilibration buffer.

Then a linear gradient from 50 ml of 20 mM sodium phosphate (pH 8.0) to 50 ml of 20 mM sodium phosphate (pH 8.0), 1M NaCl was applied.

Active fractions (measured by thrombin inhibition) were collected.

The combined active fractions were loaded onto an affinity column with immobilized thrombin (diameter 1.5 cm, height 6.5 cm, volume 11.5 ml, 60 ml/h). The column was prepared as in Example 3.

The column was equilibrated with 20 mM sodium phosphate pH 7.5. After the protein solution had been loaded onto the column it was washed with 10 column volumes of equilibration buffer until the absorption at 280 nm decreased to zero.

It was then washed with 0.5M NaCl, 20 mM sodium phosphate buffer pH 7.5. This removed non-specifically adsorbed material.

Protein specifically bound to thrombin was eluted with 0.1M glycine, 0.5M NaCl pH 2.8. The column was then immediately readjusted to pH 7.5 with phosphate buffer.

The individual fractions were neutralized with 0.1M NaOH and examined for their inhibitory action on thrombin. The fractions eluted by glycine/NaCl buffer pH 2.8 had a thrombin-inhibiting action.

The collected active fractions were, after neutralization, diluted with water (1:10) and loaded onto a Mono-Q® column (Pharmacia, volume 1 ml).

The column was equilibrated with 20 mM sodium phosphate buffer pH 7.5, 150 mM NaCl (buffer A). It was washed with buffer A until the absorption decreased to zero (10 minutes). The buffer was then changed over the course of 50 minutes to 20 mM sodium phosphate, pH 7.5, 800 mM NaCl (buffer B) (flow rate 0.5 ml/min).

Thrombin-inhibiting fractions were collected.

The collected fractions were further purified on an RP 318® (Biorad) HPLC column. The colum was equilibrated with 0.1% by weight of trifluoroacetic acid (TFA) in distilled water. The combined active fractions were loaded onto the column which was then eluted with a gradient to 0.1% by weight TFA, 100% acetonitrile at a flow rate of 1 ml/min over the course of one hour. The absorption was determined at 280 nm, and 0.5 ml fractions were collected. The collected fractions were concentrated to dryness and taken up in a phosphate-buffered saline (PBS) (0.8 g/l NaCl; 0.2 g/l HCl; 0.144 g/l sodium phosphate; 0.2 g/l potassium phosphate, pH 7.5), and the inhibitory activity was determined.

The protein was determined by the method of Bradford (Anal. Biochem., 72 (1976) (248–254) using bovine serum albumin (Boehringer Mannheim) as standard protein.

EXAMPLE 2

Determination of the inhibition of thrombin by the inhibitor

Thrombin (Boehringer Mannheim) was dissolved to a final concentration of 25 mU/ml in phosphate-buffered saline (PBS) (0.8 g/l NaCl, 0.2 g/l HCl, 0.144 g/l sodium phosphate, 0.2 g/l potassium phosphate, pH 7.5).

Chromozym TH (Boehringer Mannheim) was dissolved in 20 ml of $H_2O$ per vial.

50 μl of thrombin solution and 100 μl of Chromozym plus 25 μl of sample or buffer were placed in the wells of a microtiter plate. The absorption at 405 nm was measured at 37° C. immediately thereafter at time 0 and after 30 minutes.

When the sample was deeply colored another control without thrombin was treated as described above.

The activity of thrombin liberates a dye which absorbs at 405 nm from the chromogenic substrate. Inhibition of the thrombin by a thrombin inhibitor is evident from a smaller increase in the absorption at 405 nm and was quantified using a calibration plot.

EXAMPLE 3

Preparation of an affinity column with thrombin as ligand a) Coupling:

2 g of CNBr-activated Sepharose (Pharmacia) were washed with 200 ml of 1 mM HCl on a suction funnel. The gel was taken up in 100 mM $NaHCO_3$, 500 mM NaCl pH 8.3 and immediately mixed with 10,000 units of thrombin (Sigma) in 100 mM $NaHCO_3$, 500 mM NaCl, pH 8.3.

The solution was gently shaken at 4° C. for 24 hours.

b) Blocking:

The gel material was allowed to settle and then washed with 100 mM $NaHCO_3$, 500 mM NaCl, pH 8.3. The Sepharose was then incubated with 100 mM $NaHCO_3$, 500 mM NaCl, 1M ethanolamine pH 8.3 for 2 hours.

c) Preparation:

To remove unbound thrombin, before use the gel material is washed once more in the column with 20 column volumes of PBS pH 7.4.

EXAMPLE 4

Determination of the molecular weight by molecular sieve chromatography

Material purified by Mono-Q® chromatography was passed at a flow rate of 1 ml/min in 20 mM sodium phosphate, 150 mM NaCl, pH 7.5 through a Spherogel® TSK 3000 SW molecular sieve column (Pharmacia, diameter 7.5 mm, height 60 cm).

The reference proteins were subjected to the same procedure (serum albumin MW 67,000 Da, ovalbumin MW 45,000 Da, chymotrypsinogen A MW 25,000 Da).

The logarithm of the molecular weight of the reference proteins was plotted against their elution time.

The thrombin inhibition by the eluted fractions of the sample was determined.

The logarithm of the molecular weight of the inhibitor was obtained from the intercept of the elution time on the calibration line.

The molecular weight was found to be 20,000–24,000 dalton by this determination.

EXAMPLE 5

Determination of the molecular weight by tricine SDS polyacrylamide gel electrophoresis (Reference: Analytical Biochemistry, 166, (1987) 368–379 Tricine-Sodium Dodecyl Sulfate-Polyacrylamide Gel Electrophoresis for the Separation of Proteins in the range from 1–1000 kDa, Schägger, H. and von Jagow, G.)

The gel electrophoresis was carried out as stated in the reference at 20 mA and 1400 V, 30 watts.

The molecular weight determined by this method was 12,000±2000 dalton.

The reference proteins were intact myoglobin 17.2 kDa, myoglobin I+II 14.6 kDa, myoglobin I 8.2 kDa, myoglobin II 6.4 kDa, myoglobin III 2.6 kDa and myoglobin 1–14.

EXAMPLE 6

Determination of the sequence of the inhibitor Reduction and carboxymethylation 2.8 ml of protein solution (0.029 mg/ml) were mixed with 0.28 ml of buffer (1M tris/HCl, 0.5M guanidine hydrochloride, pH 8.6). Then 0.116 ml of dithiothreitol (DTT, 10 mg/ml) was added and the mixture was incubated at 37° C. for 10 minutes. After addition of 0.185 ml of iodoacetamide (10 mg/ml) the mixture was incubated at 37° C. for 90 minutes. The reaction was stopped with 0.073 ml of DTT as above.

The protein was purified by renewed reversed phase HPLC on RP 318®. The mixture was adjusted to a final concentration of 0.1% by weight trifluoroacetic acid (TFA) and separated in an HPLC system from Hewlett Packard (HP 1090 liquid chromatograph). The column was washed with solvent A (0.1% by weight TFA, 100% $H_2O$) for 5 minutes. Then the proportion of solvent B (90% acetonitrile, 10% $H_2O$, 0.1% by weight TFA) was increased to 50% over the course of 120 minutes. The absorption of the eluate at 214 and 280 run was measured. Absorbing fractions were collected. The protein was identified by SDS gel electrophoresis and subjected to sequence analysis in an Applied Biosystems 477 A protein sequencer in accordance with the manufacturer's instructions.

The following amino-terminal sequence was obtained (SEQ ID NO: 1):

Glu-Gly-Gly-Glu-Pro-Cys-Ala-Cys-Pro-His-Ala-Leu-His-Arg-Val-Cys-Gly-Ser-Asp

EXAMPLE 7

Determination of the isoelectric point by isoelectric focusing

The determination was carried out with an LKB Multiphor 2117 (horizontal system) and an LKB 2103 power supply. Precast gels were employed (Pharmacia Ampholine PAGplate pH 3.5–9.5). The standard proteins employed were amyloglucosidase, pH 3.5; soybean trypsin inhibitor, pH 4.55; β-lactoglobulin A, pH 5.2; bovine carbonic anhydrase, pH 5.85; human carbonic anhydrase, pH 6.55; horse myoglobin, pH 6.85 and 7.35; lentil lectin, pH 8.15, 8.45, 8.65 and trypsinogen, pH 9.3.

Focusing conditions: 1500 volts, 30 watts. Buffers:

anode 1M phosphoric acid cathode 1M sodium hydroxide solution

The plates were prefocused for 30 minutes to produce a pH gradient. The samples were loaded onto filter disks which lay on the gel. Focusing was continued for 30 minutes, the filter disks were removed and, after a further 30 minutes, focusing was stopped. The gels were immediately cut into 2 mm slices and transferred into distilled water. The protein eluted out of the gel slices overnight. The location of the thrombin inhibitor was determined by a thrombin inhibition assay. The pH can also be determined directly using a pH electrode. The reference substance hirudin had an isoelectric point at pH 3.5 and below. The novel inhibitor had an isoelectric point at pH 4.2±0.5.

EXAMPLE 8

Preparation of a DNA sequence which codes for a thrombin-inhibitory protein.

a) Isolation of RNA and preparation of a cDNA bank

Complete RNA was obtained from whole animals of the species *Rhodnius prolixus* by disruption in guanidinium thiocyanate. This was carried out using the materials and in accordance with the instructions for the RNA isolation kit supplied by Stratagene, La Jolla, Calif., USA (Catalog No. 200345). The polyadenylated messenger RNA was selected from the complete RNA by oligo(dT) affinity separation. This method was carried out with the materials and in accordance with the instructions for the PolyATract mRNA isolation system supplied by Promega, Madison, Wis., USA (Catalog No. Z5200).

The cDNA was synthesized from polyadenylated messenger RNA using materials and in accordance with the instructions of the ZAP-cDNA synthesis kit supplied by Stratagene, La Jolla, Calif., USA (Catalog No. 200400) and was then packaged in lambda phages using materials and in accordance with the instructions of the Uni-ZAP XR Giga-packII Cloning Kit supplied by Stratagene, La Jolla, Calif., USA (Catalog No. 237611).

b) Preparation of oligonucleotide probes for the PCR

The starting point for the cloning of cDNA fragments by the polymerase chain reaction (PCR, see Molecular Cloning, 2nd edition (1989), Sambrook, J. et al., CSH Press, page 14.1 et seq.) was peptides with the amino-terminal protein sequence described in Example 6 (SEQ ID NO: 1).

On the basis of the genetic code it is possible to derive from the peptide sequence SEQ ID NO: 18:

NH$_2$-Glu Gly Gly Glu Pro Cys Ala Cys Pro His Ala (pos. 1–11) the nucleic acid sequence SEQ ID NO: 19:

5'-GAA GGT GGT GAA CCN TGY GCN TGY CCN CAY GC-3' of the coding DNA strand. The known degeneracy of the genetic code means that it is possible to employ a plurality of nucleotides (N: A, C, G, T; Y: C, T;) at some positions. This means that there is a complexity of 512 different oligonucleotides during the oligonucleotide synthesis.

The syntheses were carried out with an Applied Biosystems type 360A DNA synthesizer. The oligonucleotides were, after removal of the protective groups, purified by gel electrophoresis on an acrylamide/urea gel.

c) Preparation of DNA templates for the PCR

5 μg of complete RNA or 1 μg of poly(A)$^+$ RNA from the RNA preparations detailed under a) were translated with the oligonucleotide A-B-T$_{18}$, (SEQ ID NO: 20):

5'-CGAGGGGGATGGTCGACGGAAGCGAC-CTTTTTTTTTTTTTTTTTT-3' and with the aid of the enzyme reverse transcriptase into single-strand cDNA (1°cDNA). This was carried out with the materials and in accordance with the instructions for the SuperScript preamplification system supplied by Gibco BRL, Eggenstein, Germany (Catalog No.8089SA). After the reaction was complete, the low molecular weight constituents were removed on Biospin 30 columns supplied by BioRad, Richmond, Calif., USA (Catalog No. 732-6006).

d) PCR and cloning

The polymerase chain reaction was carried out in accordance with known protocols (see Molecular Cloning, 2nd edition (1989), Sambrook, J. et al., CSH Press, page 14.1 et seq.). A Perkin Elmer DNA thermal cycler was used for this, and a modification of the internal primer principle of Frohmann, M. A. et al. (Proc. Natl. Acad. Sci. USA 85 (1988) 8998–9002) was employed.

Specifically, the 1°cDNA from c) was amplified with the oligonucleotides SEQ ID NO: 19, see above, and SEQ ID NO: 21 (from A-B-T$_{18}$):

5'-CGAGGGGGATGGTCGACGG-3'.

The PCR products were fractionated according to size by gel electrophoresis. Separated agarose slices with DNA fragments of increasing molecular weight were then employed in a second PCR with oligonucleotide SEQ ID NO: 19, see above, and SEQ ID NO: 22 (from A-B-T$_{18}$):

5'-GATGGTCGACGGAAGCGACC-3'.

The PCR products selected in this way were likewise fractionated by gel electrophoresis and eluted by standard methods. After subcloning into the EcoRV cleavage site of the vector pBluescriptKS and replication of the plasmid in *E. coli* DH5alpha, sequence analysis of a clone with SEQ ID NO: 2 revealed an open reading frame of 103 amino acids with SEQ ID NO: 3 which contains the peptide described in SEQ ID NO: 1. The clone was then called pRPTI.

e) Screening of the cDNA bank

1×10$^6$ recombinant phages of Rhodnius prolixus cDNA bank were subjected to screening with a probe corresponding to SEQ ID NO: 2. Known protocols were used for this (see "Molecular Cloning", 2nd edition (1989), Sambrook, J. et al., CSH Press). The positive clones underwent sequence analysis and are listed as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16.

f) Heterologous expression of the thrombin inhibitor

To prepare the recombinant thrombin inhibitor initially cDNA sequence SEQ ID NO: 2 coding for positions 1–103 of amino-acid sequence SEQ ID NO: 3 underwent PCR amplification by the methods described and were cloned with suitable ends in the XmnI and BamHI cleavage sites of the bacterial expression vector pMAL-p2 (Protein Fusion and Purification System, GeneExpress, New England Biolabs No. 800). This cloning leads to fusion of the bacterial maltose binding protein with the described thrombin inhibitor in the same reading frame. *E. coli* DH5alpha cells were transformed with the resulting plasmid, and the recombinant fusion protein was expressed and purified in accordance with the manufacturer's instructions. The thrombin inhibitor can be separated enzymatically from the fusion partner by utilizing a factor Xa cleavage site at the point of fusion. The yield of the thrombin inhibitor which has undergone periplasmic expression in *E. coli* is 6000 units/L of culture (standard: National Institutes of Health).

We claim:

1. An isolated and purified protein with thrombin-inhibitory action from assassin bugs of the genus Rhodnius, having an amino-acid sequence indicated in SEQ ID NO: 3.

2. An isolated and purified protein with thrombin-inhibitory action, containing one or more domains with the amino-acid sequence indicated in SEQ ID NO: 3.

3. A pharmaceutical composition comprising the protein defined in claim 1 and another anticoagulant factor.

4. A method of treating a host in need of thrombin-inhibitory activity which comprises administering to said host an effective amount of the protein defined in claim 1.

5. The method of claim 4, wherein the host is in need of treatment for a thrombosis.

\* \* \* \* \*

SEQUENCE LISTING ( 1 ) GENERAL INFORMATION:

( i i i ) NUMBER OF SEQUENCES: 22

( 2 ) INFORMATION FOR SEQ ID NO: 1:

( i ) SEQUENCE CHARACTERISTICS:
( A ) LENGTH: 19 amino acids
( B ) TYPE: amino acid
( D ) TOPOLOGY: linear ( x i ) SEQUENCE DESCRIPTION: SEQ ID NO: 1:

```
Glu  Gly  Gly  Glu  Pro  Cys  Ala  Cys  Pro  His  Ala  Leu  His  Arg  Val  Cys
 1                    5                         10                       15
Gly  Ser  Asp
```

( 2 ) INFORMATION FOR SEQ ID NO: 2:

( i ) SEQUENCE CHARACTERISTICS:
( A ) LENGTH: 350 base pairs
( B ) TYPE: nucleic acid
( C ) STRANDEDNESS: single
( D ) TOPOLOGY: linear ( x i ) SEQUENCE DESCRIPTION: SEQ ID NO: 2:

```
GAA  GGT  GGT  GAA  CCG  TGC  GCT  TGC  CCC  CAC  GCT  CTG  CAT  AGA  GTT  TGC        48
Glu  Gly  Gly  Glu  Pro  Cys  Ala  Cys  Pro  His  Ala  Leu  His  Arg  Val  Cys
 1                    5                         10                       15

GGC  TCT  GAT  GGT  GAA  ACT  TAT  AGC  AAC  CCT  TGT  ACG  CTG  AAC  TGT  GCT        96
Gly  Ser  Asp  Gly  Glu  Thr  Tyr  Ser  Asn  Pro  Cys  Thr  Leu  Asn  Cys  Ala
               20                        25                        30

AAA  TTC  AAT  GGA  AAG  CCA  GAA  CTT  GTA  AAA  GTC  CAT  GAT  GGT  CCT  TGC       144
Lys  Phe  Asn  Gly  Lys  Pro  Glu  Leu  Val  Lys  Val  His  Asp  Gly  Pro  Cys
               35                        40                        45

GAA  CCG  GAT  GAG  GAT  GAA  GAT  GTT  TGC  CAA  GAA  TGT  GAT  GGT  GAT  GAA       192
Glu  Pro  Asp  Glu  Asp  Glu  Asp  Val  Cys  Gln  Glu  Cys  Asp  Gly  Asp  Glu
      50                        55                        60

TAC  AAA  CCA  GTT  TGC  GGA  TCT  GAC  GAC  ATA  ACT  TAC  GAT  AAC  AAC  TGT       240
Tyr  Lys  Pro  Val  Cys  Gly  Ser  Asp  Asp  Ile  Thr  Tyr  Asp  Asn  Asn  Cys
 65                        70                        75                        80

CGA  CTA  GAG  TGT  GCC  TCT  ATC  TCT  TCC  AGC  CCA  GGA  GTT  GAA  CTG  AAA       288
Arg  Leu  Glu  Cys  Ala  Ser  Ile  Ser  Ser  Ser  Pro  Gly  Val  Glu  Leu  Lys
                     85                        90                        95

CAT  GAA  GGA  CCT  TGT  AGA  ACC  GAAAAAAAAA  AAAAAAAAAA  AGGTCGCTTC              339
His  Glu  Gly  Pro  Cys  Arg  Thr
               100

CGTCGACCAT C                                                                         350
```

( 2 ) INFORMATION FOR SEQ ID NO: 3:

( i ) SEQUENCE CHARACTERISTICS:
( A ) LENGTH: 103 amino acids
( B ) TYPE: amino acid
( D ) TOPOLOGY: linear ( x i ) SEQUENCE DESCRIPTION: SEQ ID NO: 3:

```
Glu  Gly  Gly  Glu  Pro  Cys  Ala  Cys  Pro  His  Ala  Leu  His  Arg  Val  Cys
 1                    5                         10                       15

Gly  Ser  Asp  Gly  Glu  Thr  Tyr  Ser  Asn  Pro  Cys  Thr  Leu  Asn  Cys  Ala
               20                        25                        30
```

```
Lys Phe Asn Gly Lys Pro Glu Leu Val Lys Val His Asp Gly Pro Cys
        35              40                  45

Glu Pro Asp Glu Asp Glu Asp Val Cys Gln Glu Cys Asp Gly Asp Glu
        50              55                  60

Tyr Lys Pro Val Cys Gly Ser Asp Asp Ile Thr Tyr Asp Asn Asn Cys
65                  70                  75                   80

Arg Leu Glu Cys Ala Ser Ile Ser Ser Ser Pro Gly Val Glu Leu Lys
                85                  90                   95

His Glu Gly Pro Cys Arg Thr
                100
```

( 2 ) INFORMATION FOR SEQ ID NO: 4:

( i ) SEQUENCE CHARACTERISTICS:
        ( A ) LENGTH: 447 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

```
AA  ACT TAT AGC AAC CCT TGT ACG CTG AAC TGT GCT AAA CAC AAT GGA       47
    Thr Tyr Ser Asn Pro Cys Thr Leu Asn Cys Ala Lys His Asn Gly
    1               5                   10                  15

AAG CCA GGT CTT GTA AAA GTC CAT GAT GGT CCT TGC GAA CCG GAT GAG       95
Lys Pro Gly Leu Val Lys Val His Asp Gly Pro Cys Glu Pro Asp Glu
                20                  25                  30

GAT GAA GAT GTT TGC CAA GAA TGT GAT GAT GTC GAT TAC GAA CCA GTT       143
Asp Glu Asp Val Cys Gln Glu Cys Asp Asp Val Asp Tyr Glu Pro Val
            35                  40                  45

TGT GGA ACT GAC GAC AAA ACT TAC GAT AAC AAC TGT CGA CTA GAG TGT       191
Cys Gly Thr Asp Asp Lys Thr Tyr Asp Asn Asn Cys Arg Leu Glu Cys
        50                  55                  60

GCC TCT ATC TCT TCC AGC CCA GGA CTT GAA CTG AAG CAC ACA GGA AAA       239
Ala Ser Ile Ser Ser Ser Pro Gly Leu Glu Leu Lys His Thr Gly Lys
    65                  70                  75

TGT CTA CCC CAT TTG GAT TTT CCC GAC CCA GTT TAAAGCTTGC ACATAACGGA     292
Cys Leu Pro His Leu Asp Phe Pro Asp Pro Val
80                  85                  90

AAATGCACTA TAGCAGAGTT ATATCACGGT TTATTGTAAA AAAAGATTAT ATGAATTTAT     352

CATAATATCA ATAAAATAGC TTATTTAAA AATATTGAAC CAATTTAAAT TTTCAACATA      412

TGTATATGTA AATAAATTTA AAAAAAAAAA AAAAA                                447
```

( 2 ) INFORMATION FOR SEQ ID NO: 5:

( i ) SEQUENCE CHARACTERISTICS:
        ( A ) LENGTH: 90 amino acids
        ( B ) TYPE: amino acid
        ( D ) TOPOLOGY: linear ( x i ) SEQUENCE DESCRIPTION: SEQ ID NO: 5:

```
Thr Tyr Ser Asn Pro Cys Thr Leu Asn Cys Ala Lys His Asn Gly Lys
1               5                   10                  15

Pro Gly Leu Val Lys Val His Asp Gly Pro Cys Glu Pro Asp Glu Asp
                20                  25                  30

Glu Asp Val Cys Gln Glu Cys Asp Asp Val Asp Tyr Glu Pro Val Cys
            35                  40                  45

Gly Thr Asp Asp Lys Thr Tyr Asp Asn Asn Cys Arg Leu Glu Cys Ala
        50                  55                  60

Ser Ile Ser Ser Ser Pro Gly Leu Glu Leu Lys His Thr Gly Lys Cys
```

```
                65                          70                          75                          80
Leu   Pro   His   Leu   Asp   Phe   Pro   Asp   Pro   Val
                        85                                90
```

( 2 ) INFORMATION FOR SEQ ID NO:6:

( i ) SEQUENCE CHARACTERISTICS:
        ( A ) LENGTH: 732 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

```
AG  CGT   CTA   CTG   TTG   TTA   CTC   GGA   TTG   GCT   GCA   CTC   GTT   GCA   GCT   GAA             47
    Arg   Leu   Leu   Leu   Leu   Leu   Gly   Leu   Ala   Ala   Leu   Val   Ala   Ala   Glu
    -14               -10                                 -5                                  1

GGG   GGG   GAA   CCA   TGC   GCA   TGT   CCA   CAT   GCT   CTG   CAT   AGA   GTT   TGC   GGC           95
Gly   Gly   Glu   Pro   Cys   Ala   Cys   Pro   His   Ala   Leu   His   Arg   Val   Cys   Gly
                  5                             10                              15

TCT   GAT   GGT   GAA   ACT   TAT   AGC   AAC   CCT   TGT   ACG   CTG   AAC   TGT   GCT   AAA          143
Ser   Asp   Gly   Glu   Thr   Tyr   Ser   Asn   Pro   Cys   Thr   Leu   Asn   Cys   Ala   Lys
            20                            25                            30

TTC   AAT   GGC   AAG   CCA   GAA   CTT   GTA   AAA   GTC   CAT   GAT   GGT   CCT   TGC   GAA          191
Phe   Asn   Gly   Lys   Pro   Glu   Leu   Val   Lys   Val   His   Asp   Gly   Pro   Cys   Glu
      35                            40                            45

CCG   GAT   GAG   GAT   GAA   GAT   GTT   TGC   CAA   GAA   TGT   GAT   GGT   GAT   GAA   TAC          239
Pro   Asp   Glu   Asp   Glu   Asp   Val   Cys   Gln   Glu   Cys   Asp   Gly   Asp   Glu   Tyr
50                            55                            60                            65

AAA   CCA   GTT   TGC   GGA   TCT   GAC   GGC   ATA   ACT   TAC   GAT   AAC   AAC   TGT   CGA          287
Lys   Pro   Val   Cys   Gly   Ser   Asp   Gly   Ile   Thr   Tyr   Asp   Asn   Asn   Cys   Arg
                        70                            75                            80

CTA   GAG   TGT   GCC   TCT   ATC   TCT   TCC   AGC   CCA   GGA   GTT   GAA   CTG   AAA   CAT          335
Leu   Glu   Cys   Ala   Ser   Ile   Ser   Ser   Ser   Pro   Gly   Val   Glu   Leu   Lys   His
                  85                            90                            95

GAA   GGG   ATA   TGT   AGA   AAG   GAG   GAA   AAG   AAA   CTT   CCT   AAA   AGA   TCT   GTG          383
Glu   Gly   Ile   Cys   Arg   Lys   Glu   Glu   Lys   Lys   Leu   Pro   Lys   Arg   Ser   Val
            100                           105                           110

GGA   TTG   GAA   CAT   ACA   TGC   GTC   TGT   CCT   TAT   AAT   TAT   TTC   CCG   GTT   TGC          431
Gly   Leu   Glu   His   Thr   Cys   Val   Cys   Pro   Tyr   Asn   Tyr   Phe   Pro   Val   Cys
      115                           120                           125

GGA   ACA   GAT   GGG   GAA   ACC   TAT   CCC   AAC   TTG   TGC   GCC   CTC   CAA   TGT   CGT          479
Gly   Thr   Asp   Gly   Glu   Thr   Tyr   Pro   Asn   Leu   Cys   Ala   Leu   Gln   Cys   Arg
130                           135                           140                           145

ATG   AGA   GAA   GTT   CCA   GGA   CTT   GAA   CTG   AAG   CAC   ACA   GGA   AAA   TGT   CTA          527
Met   Arg   Glu   Val   Pro   Gly   Leu   Glu   Leu   Lys   His   Thr   Gly   Lys   Cys   Leu
                        150                           155                           160

CCC   CAT   TTG   GAT   TTT   CCC   GAC   CCA   GTT   TAAAGCTTGC  ACATAACGGA                           574
Pro   His   Leu   Asp   Phe   Pro   Asp   Pro   Val
                  165                           170

AAATGCACTA    TAGCAGAGTT    ATATCACGGT    TTATTGTAAA    AAAAGATTAT    ATGAATTTAT                       634

CATAATATCA    ATAAAATAGC    TTATTTAAA     AATATTGAAC    CAATTTAAAT    TTTCAACATA                       694

TGTATATGTA    AATAAATTTA    AAAAAAAAAA    AAAAAAA                                                      732
```

( 2 ) INFORMATION FOR SEQ ID NO: 7:

( i ) SEQUENCE CHARACTERISTICS:
        ( A ) LENGTH: 184 amino acids
        ( B ) TYPE: amino acid
        ( D ) TOPOLOGY: linear ( x i ) SEQUENCE DESCRIPTION: SEQ ID NO: 7:

| | | | | | | | | | | | | | | |
|---|---|---|---|---|---|---|---|---|---|---|---|---|---|---|
| Arg | Leu | Leu | Leu | Leu | Leu | Gly | Leu | Ala | Ala | Leu | Val | Ala | Ala | Glu | Gly |
| -14 | | | | -10 | | | | | -5 | | | | | | 1 |

| Gly | Glu | Pro | Cys | Ala | Cys | Pro | His | Ala | Leu | His | Arg | Val | Cys | Gly | Ser |
|---|---|---|---|---|---|---|---|---|---|---|---|---|---|---|---|
| | | 5 | | | | | 10 | | | | | 15 | | | |

| Asp | Gly | Glu | Thr | Tyr | Ser | Asn | Pro | Cys | Thr | Leu | Asn | Cys | Ala | Lys | Phe |
|---|---|---|---|---|---|---|---|---|---|---|---|---|---|---|---|
| | | 20 | | | | 25 | | | | | 30 | | | | |

| Asn | Gly | Lys | Pro | Glu | Leu | Val | Lys | Val | His | Asp | Gly | Pro | Cys | Glu | Pro |
|---|---|---|---|---|---|---|---|---|---|---|---|---|---|---|---|
| 35 | | | | | 40 | | | | 45 | | | | | | 50 |

| Asp | Glu | Asp | Glu | Asp | Val | Cys | Gln | Glu | Cys | Asp | Gly | Asp | Glu | Tyr | Lys |
|---|---|---|---|---|---|---|---|---|---|---|---|---|---|---|---|
| | | | | 55 | | | | | 60 | | | | | 65 | |

| Pro | Val | Cys | Gly | Ser | Asp | Gly | Ile | Thr | Tyr | Asp | Asn | Asn | Cys | Arg | Leu |
|---|---|---|---|---|---|---|---|---|---|---|---|---|---|---|---|
| | | | 70 | | | | | 75 | | | | | 80 | | |

| Glu | Cys | Ala | Ser | Ile | Ser | Ser | Ser | Pro | Gly | Val | Glu | Leu | Lys | His | Glu |
|---|---|---|---|---|---|---|---|---|---|---|---|---|---|---|---|
| | | 85 | | | | | 90 | | | | | 95 | | | |

| Gly | Ile | Cys | Arg | Lys | Glu | Glu | Lys | Lys | Leu | Pro | Lys | Arg | Ser | Val | Gly |
|---|---|---|---|---|---|---|---|---|---|---|---|---|---|---|---|
| | | 100 | | | | 105 | | | | | 110 | | | | |

| Leu | Glu | His | Thr | Cys | Val | Cys | Pro | Tyr | Asn | Tyr | Phe | Pro | Val | Cys | Gly |
|---|---|---|---|---|---|---|---|---|---|---|---|---|---|---|---|
| 115 | | | | | 120 | | | | | 125 | | | | | 130 |

| Thr | Asp | Gly | Glu | Thr | Tyr | Pro | Asn | Leu | Cys | Ala | Leu | Gln | Cys | Arg | Met |
|---|---|---|---|---|---|---|---|---|---|---|---|---|---|---|---|
| | | | | 135 | | | | | 140 | | | | | 145 | |

| Arg | Glu | Val | Pro | Gly | Leu | Glu | Leu | Lys | His | Thr | Gly | Lys | Cys | Leu | Pro |
|---|---|---|---|---|---|---|---|---|---|---|---|---|---|---|---|
| | | | 150 | | | | | 155 | | | | | 160 | | |

| His | Leu | Asp | Phe | Pro | Asp | Pro | Val |
|---|---|---|---|---|---|---|---|
| | | 165 | | | | | 170 |

(2) INFORMATION FOR SEQ ID NO: 8:

(i) SEQUENCE CHARACTERISTICS:
  (A) LENGTH: 677 base pairs
  (B) TYPE: nucleic acid
  (C) STRANDEDNESS: single
  (D) TOPOLOGY: linear (xi) SEQUENCE DESCRIPTION: SEQ ID NO: 8:

| ATG | AAG | CGT | CTA | CTG | TTG | TTA | CTC | GGA | TTG | GCT | GCA | CTC | GTT | GCA | GCT | 48 |
|---|---|---|---|---|---|---|---|---|---|---|---|---|---|---|---|---|
| Met | Lys | Arg | Leu | Leu | Leu | Leu | Leu | Gly | Leu | Ala | Ala | Leu | Val | Ala | Ala | |
| -15 | | | | | -10 | | | | | -5 | | | | | | |

| GAA | GGG | GGG | GAA | CCA | TGC | GCA | TGT | CCA | CAT | GCT | CTG | CAT | AGA | GTT | TGC | 96 |
|---|---|---|---|---|---|---|---|---|---|---|---|---|---|---|---|---|
| Glu | Gly | Gly | Glu | Pro | Cys | Ala | Cys | Pro | His | Ala | Leu | His | Arg | Val | Cys | |
| 1 | | | | 5 | | | | | 10 | | | | | 15 | | |

| GGC | TCT | GAT | GGT | GAA | ACT | TAT | AGC | AAC | CCT | TGT | ACG | CTG | AAC | TGT | GCT | 144 |
|---|---|---|---|---|---|---|---|---|---|---|---|---|---|---|---|---|
| Gly | Ser | Asp | Gly | Glu | Thr | Tyr | Ser | Asn | Pro | Cys | Thr | Leu | Asn | Cys | Ala | |
| | | | 20 | | | | | 25 | | | | | 30 | | | |

| AAA | TTT | AAT | GGA | AAG | CCA | GAA | CTT | GTA | AAA | GTC | CAT | GAT | GGT | CCT | TGC | 192 |
|---|---|---|---|---|---|---|---|---|---|---|---|---|---|---|---|---|
| Lys | Phe | Asn | Gly | Lys | Pro | Glu | Leu | Val | Lys | Val | His | Asp | Gly | Pro | Cys | |
| | | 35 | | | | | 40 | | | | | 45 | | | | |

| GAA | CCG | GAT | GAG | GAT | GAA | GAT | GTT | TGC | CAA | GAA | TGT | GAT | GGT | GAT | GAA | 240 |
|---|---|---|---|---|---|---|---|---|---|---|---|---|---|---|---|---|
| Glu | Pro | Asp | Glu | Asp | Glu | Asp | Val | Cys | Gln | Glu | Cys | Asp | Gly | Asp | Glu | |
| | 50 | | | | | 55 | | | | | 60 | | | | | |

| TAC | AAA | CCA | GTT | TGC | GGA | TCT | GAC | GGC | ATA | ACT | TAC | GAT | AAC | AAC | TGT | 288 |
|---|---|---|---|---|---|---|---|---|---|---|---|---|---|---|---|---|
| Tyr | Lys | Pro | Val | Cys | Gly | Ser | Asp | Gly | Ile | Thr | Tyr | Asp | Asn | Asn | Cys | |
| 65 | | | | | 70 | | | | | 75 | | | | | 80 | |

| CGA | CTA | GAG | TGT | GCC | TCT | ATC | TCT | TCC | AGC | CCA | GGA | GTT | GAA | CTG | AAA | 336 |
|---|---|---|---|---|---|---|---|---|---|---|---|---|---|---|---|---|
| Arg | Leu | Glu | Cys | Ala | Ser | Ile | Ser | Ser | Ser | Pro | Gly | Val | Glu | Leu | Lys | |
| | | | | 85 | | | | | 90 | | | | | 95 | | |

| CAT | GAA | GGG | ATA | TGT | AGA | AAG | GAG | GAA | AAG | AAA | CTT | CCT | AAA | AGA | TCT | 384 |
|---|---|---|---|---|---|---|---|---|---|---|---|---|---|---|---|---|
| His | Glu | Gly | Ile | Cys | Arg | Lys | Glu | Glu | Lys | Lys | Leu | Pro | Lys | Arg | Ser | |
| | | | 100 | | | | | 105 | | | | | 110 | | | |

| GTG | GGA | TTG | GAA | CAT | ACA | TGC | GTC | TGT | CCT | TAT | AAT | TAT | TTC | CCG | GTT | 432 |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Val | Gly | Leu | Glu | His | Thr | Cys | Val | Cys | Pro | Tyr | Asn | Tyr | Phe | Pro | Val |  |
|  |  | 115 |  |  |  |  | 120 |  |  |  |  | 125 |  |  |  |  |
| TGC | GGA | ACA | GAT | GGG | GAA | ACC | TAT | CCC | AAC | TTG | TGC | GCC | CTC | CAA | TGT | 480 |
| Cys | Gly | Thr | Asp | Gly | Glu | Thr | Tyr | Pro | Asn | Leu | Cys | Ala | Leu | Gln | Cys |  |
|  | 130 |  |  |  |  | 135 |  |  |  |  | 140 |  |  |  |  |  |
| CGT | ATG | AGA | GAA | GTT | CCA | GGA | CTT | GAA | CTG | AAG | CAC | ACA | GGA | AAA | TGT | 528 |
| Arg | Met | Arg | Glu | Val | Pro | Gly | Leu | Glu | Leu | Lys | His | Thr | Gly | Lys | Cys |  |
| 145 |  |  |  |  | 150 |  |  |  |  | 155 |  |  |  |  | 160 |  |
| CTA | CCC | CAT | TTG | GAT | TTT | CCC | GAC | CCA | GTT | TAAAGCTTGC | ACATAACGGA |  |  |  |  | 578 |
| Leu | Pro | His | Leu | Asp | Phe | Pro | Asp | Pro | Val |  |  |  |  |  |  |  |
|  |  |  | 165 |  |  |  |  | 170 |  |  |  |  |  |  |  |  |
| AAATGCACTA | TAGCAGAGTT | ATATCACGGT | TTATTGTAAA | AAAAGGATTA | TATGAATTTA |  |  |  |  |  |  |  |  |  |  | 638 |
| TCATAATATC | AATAAAATAG | CTTATTTTAA | AAATATTGA |  |  |  |  |  |  |  |  |  |  |  |  | 677 |

(2) INFORMATION FOR SEQ ID NO: 9:

(i) SEQUENCE CHARACTERISTICS:
        (A) LENGTH: 186 amino acids
        (B) TYPE: amino acid
        (D) TOPOLOGY: linear (xi) SEQUENCE DESCRIPTION: SEQ ID NO: 9:

|     |     |     |     |     |     |     |     |     |     |     |     |     |     |     |
| --- | --- | --- | --- | --- | --- | --- | --- | --- | --- | --- | --- | --- | --- | --- |
| Met | Lys | Arg | Leu | Leu | Leu | Leu | Leu | Gly | Leu | Ala | Ala | Leu | Val | Ala | Ala |
|  | -15 |  |  |  |  | -10 |  |  |  |  | -5 |  |  |  |  |
| Glu | Gly | Gly | Glu | Pro | Cys | Ala | Cys | Pro | His | Ala | Leu | His | Arg | Val | Cys |
| 1 |  |  |  | 5 |  |  |  |  | 10 |  |  |  |  | 15 |  |
| Gly | Ser | Asp | Gly | Glu | Thr | Tyr | Ser | Asn | Pro | Cys | Thr | Leu | Asn | Cys | Ala |
|  |  |  | 20 |  |  |  |  | 25 |  |  |  |  | 30 |  |  |
| Lys | Phe | Asn | Gly | Lys | Pro | Glu | Leu | Val | Lys | Val | His | Asp | Gly | Pro | Cys |
|  |  | 35 |  |  |  |  | 40 |  |  |  |  | 45 |  |  |  |
| Glu | Pro | Asp | Glu | Asp | Glu | Asp | Val | Cys | Gln | Glu | Cys | Asp | Gly | Asp | Glu |
|  | 50 |  |  |  |  | 55 |  |  |  |  | 60 |  |  |  |  |
| Tyr | Lys | Pro | Val | Cys | Gly | Ser | Asp | Gly | Ile | Thr | Tyr | Asp | Asn | Asn | Cys |
| 65 |  |  |  |  | 70 |  |  |  |  | 75 |  |  |  |  | 80 |
| Arg | Leu | Glu | Cys | Ala | Ser | Ile | Ser | Ser | Ser | Pro | Gly | Val | Glu | Leu | Lys |
|  |  |  |  | 85 |  |  |  |  | 90 |  |  |  |  | 95 |  |
| His | Glu | Gly | Ile | Cys | Arg | Lys | Glu | Glu | Lys | Lys | Leu | Pro | Lys | Arg | Ser |
|  |  |  |  | 100 |  |  |  | 105 |  |  |  |  | 110 |  |  |
| Val | Gly | Leu | Glu | His | Thr | Cys | Val | Cys | Pro | Tyr | Asn | Tyr | Phe | Pro | Val |
|  |  | 115 |  |  |  |  | 120 |  |  |  |  | 125 |  |  |  |
| Cys | Gly | Thr | Asp | Gly | Glu | Thr | Tyr | Pro | Asn | Leu | Cys | Ala | Leu | Gln | Cys |
|  | 130 |  |  |  |  | 135 |  |  |  |  | 140 |  |  |  |  |
| Arg | Met | Arg | Glu | Val | Pro | Gly | Leu | Glu | Leu | Lys | His | Thr | Gly | Lys | Cys |
| 145 |  |  |  |  | 150 |  |  |  |  | 155 |  |  |  |  | 160 |
| Leu | Pro | His | Leu | Asp | Phe | Pro | Asp | Pro | Val |  |  |  |  |  |  |
|  |  |  | 165 |  |  |  |  | 170 |  |  |  |  |  |  |  |

(2) INFORMATION FOR SEQ ID NO: 10:

(i) SEQUENCE CHARACTERISTICS:
        (A) LENGTH: 566 base pairs
        (B) TYPE: nucleic acid
        (C) STRANDEDNESS: single
        (D) TOPOLOGY: linear (xi) SEQUENCE DESCRIPTION: SEQ ID NO: 10:

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| A | AAA | GTC | CAT | GAT | GGT | CCT | TGC | GAA | CCG | GAT | GAG | GAT | GAA | GAT | GTT | 46 |
|  | Lys | Val | His | Asp | Gly | Pro | Cys | Glu | Pro | Asp | Glu | Asp | Glu | Asp | Val |  |
|  | 1 |  |  |  | 5 |  |  |  |  | 10 |  |  |  |  | 15 |  |

| | | | | | | | | | | | | | | | | |
|---|---|---|---|---|---|---|---|---|---|---|---|---|---|---|---|---|
| TGC | CAA | GAA | TGT | GAT | GAT | GTC | GAT | TAC | GAA | CCA | GTT | TGT | GGA | ACT | GAC | 94 |
| Cys | Gln | Glu | Cys | Asp | Asp | Val | Asp | Tyr | Glu | Pro | Val | Cys | Gly | Thr | Asp | |
| | | | | 20 | | | | | 25 | | | | | 30 | | |
| GAC | AAA | ACT | TAC | GAT | AAC | AAC | TGT | CGA | CTA | GAG | TGT | GCC | TCT | ATC | TCT | 142 |
| Asp | Lys | Thr | Tyr | Asp | Asn | Asn | Cys | Arg | Leu | Glu | Cys | Ala | Ser | Ile | Ser | |
| | | | 35 | | | | | 40 | | | | | 45 | | | |
| TCC | AGC | CCA | GGA | GTT | GAA | CTG | AAA | CAT | GAA | GGG | ATA | TGT | AGA | AAG | GAG | 190 |
| Ser | Ser | Pro | Gly | Val | Glu | Leu | Lys | His | Glu | Gly | Ile | Cys | Arg | Lys | Glu | |
| | | 50 | | | | | 55 | | | | | 60 | | | | |
| GAA | AAG | AAA | CTT | CCT | AAA | AGA | TCT | GTG | GGA | TTG | GAA | CAT | ACA | TGC | GTC | 238 |
| Glu | Lys | Lys | Leu | Pro | Lys | Arg | Ser | Val | Gly | Leu | Glu | His | Thr | Cys | Val | |
| | 65 | | | | | 70 | | | | | 75 | | | | | |
| TGT | CCT | TAT | AAT | TAT | TTC | CCG | GTT | TGC | GGA | ACA | GAT | GGG | GAA | ACC | TAT | 286 |
| Cys | Pro | Tyr | Asn | Tyr | Phe | Pro | Val | Cys | Gly | Thr | Asp | Gly | Glu | Thr | Tyr | |
| 80 | | | | | 85 | | | | | 90 | | | | | 95 | |
| CCC | AAC | TTG | TGC | GCC | CTC | CAA | TGT | CGT | ATG | AGA | GAA | GTT | CCA | GGA | CTT | 334 |
| Pro | Asn | Leu | Cys | Ala | Leu | Gln | Cys | Arg | Met | Arg | Glu | Val | Pro | Gly | Leu | |
| | | | | 100 | | | | | 105 | | | | | 110 | | |
| GAA | CTG | AAG | CAC | ACA | GGA | AAA | TGT | CTA | CCC | CAT | TTG | GAT | TTT | CCC | GAC | 382 |
| Glu | Leu | Lys | His | Thr | Gly | Lys | Cys | Leu | Pro | His | Leu | Asp | Phe | Pro | Asp | |
| | | | 115 | | | | | 120 | | | | | 125 | | | |
| CCA | GTT | TAAAGCTTGC | ACATAACGGA | AAATGCACTA | TAGCAGAGGT | ATATCACGGT | | | | | | | | | | 438 |
| Pro | Val | | | | | | | | | | | | | | | |
| | | 130 | | | | | | | | | | | | | | |

TTATTGTAAA AAAAGGTTAT ATGAATTTAT CATAATATCA ATTAAAATAG CTTATTTTAA      498

AAATATTGCC CATTTAAATT TTCAACATAT GTATATGTAA ATAAATTTAA AAAAAAAAA      558

AAAAAAAA                                                              566

( 2 ) INFORMATION FOR SEQ ID NO: 11:

( i ) SEQUENCE CHARACTERISTICS:
        ( A ) LENGTH: 129 amino acids
        ( B ) TYPE: amino acid
        ( D ) TOPOLOGY: linear ( x i ) SEQUENCE DESCRIPTION: SEQ ID NO: 11:

| | | | | | | | | | | | | | | |
|---|---|---|---|---|---|---|---|---|---|---|---|---|---|---|
| Lys | Val | His | Asp | Gly | Pro | Cys | Glu | Pro | Asp | Glu | Asp | Val | Cys |
| 1 | | | | 5 | | | | | 10 | | | | | 15 |
| Gln | Glu | Cys | Asp | Asp | Val | Asp | Tyr | Glu | Pro | Val | Cys | Gly | Thr | Asp | Asp |
| | | | | 20 | | | | | 25 | | | | | 30 | |
| Lys | Thr | Tyr | Asp | Asn | Asn | Cys | Arg | Leu | Glu | Cys | Ala | Ser | Ile | Ser | Ser |
| | | | 35 | | | | | 40 | | | | | 45 | | |
| Ser | Pro | Gly | Val | Glu | Leu | Lys | His | Glu | Gly | Ile | Cys | Arg | Lys | Glu | Glu |
| | | 50 | | | | | 55 | | | | | 60 | | | |
| Lys | Lys | Leu | Pro | Lys | Arg | Ser | Val | Gly | Leu | Glu | His | Thr | Cys | Val | Cys |
| 65 | | | | | 70 | | | | | 75 | | | | | 80 |
| Pro | Tyr | Asn | Tyr | Phe | Pro | Val | Cys | Gly | Thr | Asp | Gly | Glu | Thr | Tyr | Pro |
| | | | | 85 | | | | | 90 | | | | | 95 | |
| Asn | Leu | Cys | Ala | Leu | Gln | Cys | Arg | Met | Arg | Glu | Val | Pro | Gly | Leu | Glu |
| | | | 100 | | | | | 105 | | | | | 110 | | |
| Leu | Lys | His | Thr | Gly | Lys | Cys | Leu | Pro | His | Leu | Asp | Phe | Pro | Asp | Pro |
| | | | 115 | | | | | 120 | | | | | 125 | | |
| Val | | | | | | | | | | | | | | | |

( 2 ) INFORMATION FOR SEQ ID NO: 12:

( i ) SEQUENCE CHARACTERISTICS:
        ( A ) LENGTH: 326 base pairs
        ( B ) TYPE: nucleic acid (C) STRANDEDNESS: single
(D) TOPOLOGY: linear (xi) SEQUENCE DESCRIPTION: SEQ ID NO: 12:

| GTC | GAT | TAC | GAA | CCA | GTT | TGT | GGA | ACT | GAC | GAC | AAA | ACT | TAC | GAT | AAC | 48 |
| Val | Asp | Tyr | Glu | Pro | Val | Cys | Gly | Thr | Asp | Asp | Lys | Thr | Tyr | Asp | Asn | |
| 1 | | | | 5 | | | | | 10 | | | | | 15 | | |

| AAC | TGT | CGA | CTA | GAG | TGT | GCC | TCT | ATC | TCT | TCC | AGC | CCA | GGA | GTT | GAA | 96 |
| Asn | Cys | Arg | Leu | Glu | Cys | Ala | Ser | Ile | Ser | Ser | Ser | Pro | Gly | Val | Glu | |
| | | | 20 | | | | | 25 | | | | | 30 | | | |

| CTG | AAA | CAT | GAA | GGG | ATA | TGT | AGA | AAG | GAG | GAA | AAG | AAA | CTT | CCT | AAA | 144 |
| Leu | Lys | His | Glu | Gly | Ile | Cys | Arg | Lys | Glu | Glu | Lys | Lys | Leu | Pro | Lys | |
| | | 35 | | | | | 40 | | | | | 45 | | | | |

| AGA | TCT | GTG | GGA | TTG | GAA | CAT | ACA | TGC | GTC | TGT | CCT | TAT | AAT | TAT | TTC | 192 |
| Arg | Ser | Val | Gly | Leu | Glu | His | Thr | Cys | Val | Cys | Pro | Tyr | Asn | Tyr | Phe | |
| | 50 | | | | | 55 | | | | | 60 | | | | | |

| CCG | GTT | TGC | GGA | ACA | GAT | GGG | GAA | ACC | TAT | CCC | AAC | TTG | TGC | GGC | CTC | 240 |
| Pro | Val | Cys | Gly | Thr | Asp | Gly | Glu | Thr | Tyr | Pro | Asn | Leu | Cys | Gly | Leu | |
| 65 | | | | | 70 | | | | | 75 | | | | | 80 | |

| CAA | TGT | CGT | ATG | AGA | GAA | GTT | CCA | GGA | CTT | GAA | CTG | AAG | CAC | ACA | GGA | 288 |
| Gln | Cys | Arg | Met | Arg | Glu | Val | Pro | Gly | Leu | Glu | Leu | Lys | His | Thr | Gly | |
| | | | | 85 | | | | | 90 | | | | | 95 | | |

| AAA | TGT | CTA | CCC | CAT | TTG | GAT | TTT | CCC | GAC | CCA | GTT | TA | | | | 326 |
| Lys | Cys | Leu | Pro | His | Leu | Asp | Phe | Pro | Asp | Pro | Val | | | | | |
| | | | 100 | | | | | 105 | | | | | | | | |

(2) INFORMATION FOR SEQ ID NO: 13:

(i) SEQUENCE CHARACTERISTICS:
        (A) LENGTH: 108 amino acids
        (B) TYPE: amino acid
        (D) TOPOLOGY: linear (xi) SEQUENCE DESCRIPTION: SEQ ID NO: 13:

| Val | Asp | Tyr | Glu | Pro | Val | Cys | Gly | Thr | Asp | Asp | Lys | Thr | Tyr | Asp | Asn |
| 1 | | | | 5 | | | | | 10 | | | | | 15 | |

| Asn | Cys | Arg | Leu | Glu | Cys | Ala | Ser | Ile | Ser | Ser | Ser | Pro | Gly | Val | Glu |
| | | | 20 | | | | | 25 | | | | | 30 | | |

| Leu | Lys | His | Glu | Gly | Ile | Cys | Arg | Lys | Glu | Glu | Lys | Lys | Leu | Pro | Lys |
| | | 35 | | | | | 40 | | | | | 45 | | | |

| Arg | Ser | Val | Gly | Leu | Glu | His | Thr | Cys | Val | Cys | Pro | Tyr | Asn | Tyr | Phe |
| | 50 | | | | | 55 | | | | | 60 | | | | |

| Pro | Val | Cys | Gly | Thr | Asp | Gly | Glu | Thr | Tyr | Pro | Asn | Leu | Cys | Gly | Leu |
| 65 | | | | | 70 | | | | | 75 | | | | | 80 |

| Gln | Cys | Arg | Met | Arg | Glu | Val | Pro | Gly | Leu | Glu | Leu | Lys | His | Thr | Gly |
| | | | | 85 | | | | | 90 | | | | | 95 | |

| Lys | Cys | Leu | Pro | His | Leu | Asp | Phe | Pro | Asp | Pro | Val |
| | | | 100 | | | | | 105 | | | |

(2) INFORMATION FOR SEQ ID NO: 14:

(i) SEQUENCE CHARACTERISTICS:
        (A) LENGTH: 616 base pairs
        (B) TYPE: nucleic acid
        (C) STRANDEDNESS: single
        (D) TOPOLOGY: linear (xi) SEQUENCE DESCRIPTION: SEQ ID NO: 14:

| G | CGT | CTA | CTG | TTG | TTA | CTC | GGA | TTG | GCT | GCA | CTC | GTT | GCA | GCT | GAA | 46 |
| | Arg | Leu | Leu | Leu | Leu | Leu | Gly | Leu | Ala | Ala | Leu | Val | Ala | Ala | Glu | |
| | −14 | | | | −10 | | | | | −5 | | | | | 1 | |

| GGG | GGG | GAA | CCA | TGC | GCA | TGT | CCA | CAT | GCT | CTG | CAT | AGA | GTT | TGC | GGC | 94 |

| | | | | | | | | | | | | | | | | |
|---|---|---|---|---|---|---|---|---|---|---|---|---|---|---|---|---|
|Gly|Gly|Glu|Pro|Cys|Ala|Cys|Pro|His|Ala|Leu|His|Arg|Val|Cys|Gly| |
| | | |5| | | |  |10| | | | |15| | | |

```
TCT GAT GGT GAA ACT TAT AGC AAC CCT TGT ACG CTG AAC TGT GCT AAA       142
Ser Asp Gly Glu Thr Tyr Ser Asn Pro Cys Thr Leu Asn Cys Ala Lys
        20              25                  30

TTC AAT GGA AAG CCA GAA CTT GTA AAA GTC CAT GAT GGT CCT TGC GAA       190
Phe Asn Gly Lys Pro Glu Leu Val Lys Val His Asp Gly Pro Cys Glu
    35              40              45

CCG GAT GAG GAT GAA GAT GTT TGC CAA GAA TGT GAT GAT GTC GAT TAC       238
Pro Asp Glu Asp Glu Asp Val Cys Gln Glu Cys Asp Asp Val Asp Tyr
50              55              60                              65

GAA CCA GTT TGT GGA ACT GAC GAC AAA ACT TAC GAT AAC AAC TGT CGA       286
Glu Pro Val Cys Gly Thr Asp Asp Lys Thr Tyr Asp Asn Asn Cys Arg
                70              75                      80

CTA GAG TGT GCC TCT ATC TCT TCC AGC CCA GGA GTT GAA CTG AAA CAT       334
Leu Glu Cys Ala Ser Ile Ser Ser Ser Pro Gly Val Glu Leu Lys His
            85              90              95

GAA GGG ATA TGT AGA AAG GAG GAA AAG AAA CTT CCT AAA AGA TCT GTG       382
Glu Gly Ile Cys Arg Lys Glu Glu Lys Lys Leu Pro Lys Arg Ser Val
        100             105             110

GGA TTG GAA CAT ACA TGC GTC TGT CCT TAT AAT TAT TTC CCG GTT TGC       430
Gly Leu Glu His Thr Cys Val Cys Pro Tyr Asn Tyr Phe Pro Val Cys
115             120             125

GGA ACA GAT GGG GAA ACC TAT CCC AAC TTG TGC GCC CTC CAA TGT CGT       478
Gly Thr Asp Gly Glu Thr Tyr Pro Asn Leu Cys Ala Leu Gln Cys Arg
130             135                 140                 145

ATG AGA GAA GTT CCA GGA CTT GAA CTG AAG CAC ACA GGA AAA TGT CTA       526
Met Arg Glu Val Pro Gly Leu Glu Leu Lys His Thr Gly Lys Cys Leu
                150                 155                 160

CCC CAT TTG GAT TTT CCC GAC CCA GTT TAAAGCTTGC ACATAACGGA            573
Pro His Leu Asp Phe Pro Asp Pro Val
                165                 170

AAATGCACTA TAGCAGAGTT ATATCACGGT TTATTGTAAA AAA                      616
```

( 2 ) INFORMATION FOR SEQ ID NO: 15:

( i ) SEQUENCE CHARACTERISTICS:
( A ) LENGTH: 184 amino acids
( B ) TYPE: amino acid
( D ) TOPOLOGY: linear ( x i ) SEQUENCE DESCRIPTION: SEQ ID NO: 15:

```
Arg Leu Leu Leu Leu Leu Gly Leu Ala Ala Leu Val Ala Ala Glu Gly
-14             -10                 -5                      1

Gly Glu Pro Cys Ala Cys Pro His Ala Leu His Arg Val Cys Gly Ser
        5                   10                  15

Asp Gly Glu Thr Tyr Ser Asn Pro Cys Thr Leu Asn Cys Ala Lys Phe
        20              25                  30

Asn Gly Lys Pro Glu Leu Val Lys Val His Asp Gly Pro Cys Glu Pro
35              40                  45                      50

Asp Glu Asp Glu Asp Val Cys Gln Glu Cys Asp Asp Val Asp Tyr Glu
            55                  60                      65

Pro Val Cys Gly Thr Asp Asp Lys Thr Tyr Asp Asn Asn Cys Arg Leu
        70                  75                  80

Glu Cys Ala Ser Ile Ser Ser Ser Pro Gly Val Glu Leu Lys His Glu
            85              90                  95

Gly Ile Cys Arg Lys Glu Glu Lys Lys Leu Pro Lys Arg Ser Val Gly
        100             105                 110

Leu Glu His Thr Cys Val Cys Pro Tyr Asn Tyr Phe Pro Val Cys Gly
```

| | | | | 115 | | | | | 120 | | | | | 125 | | | | | 130 | |
|---|---|---|---|---|---|---|---|---|---|---|---|---|---|---|---|---|---|---|---|---|
| Thr | Asp | Gly | Glu | Thr | Tyr | Pro | Asn | Leu | Cys | Ala | Leu | Gln | Cys | Arg | Met |
| | | | | 135 | | | | | 140 | | | | | 145 | |

| Arg | Glu | Val | Pro | Gly | Leu | Glu | Leu | Lys | His | Thr | Gly | Lys | Cys | Leu | Pro |
|---|---|---|---|---|---|---|---|---|---|---|---|---|---|---|---|
| | | | 150 | | | | | 155 | | | | | 160 | | |

| His | Leu | Asp | Phe | Pro | Asp | Pro | Val |
|---|---|---|---|---|---|---|---|
| | | 165 | | | | | 170 |

( 2 ) INFORMATION FOR SEQ ID NO: 16:

( i ) SEQUENCE CHARACTERISTICS:
        ( A ) LENGTH: 1282 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 16:

```
AG CGT CTA CTG TTG TTA CTC GGA TTG GCT GCA CTC GTT GCA GCT GAA            47
   Arg Leu Leu Leu Leu Leu Gly Leu Ala Ala Leu Val Ala Ala Glu
   -14             -10                  -5                    1

GGG GGG GAA CCA TGC GCA TGT CCA CAT GCT CTG CAT AGA GTT TGC GGC           95
Gly Gly Glu Pro Cys Ala Cys Pro His Ala Leu His Arg Val Cys Gly
            5                   10                      15

TCT GAT GGT GAA ACT TAT AGC AAC CCT TGT ACG CTG AAC TGT GCT AAA          143
Ser Asp Gly Glu Thr Tyr Ser Asn Pro Cys Thr Leu Asn Cys Ala Lys
        20                  25                  30

TTC AAT GGA AAG CCA GAA CTT GTA AAA GTC CAT GAT GGT CCT TGC GAA          191
Phe Asn Gly Lys Pro Glu Leu Val Lys Val His Asp Gly Pro Cys Glu
    35                  40                  45

CCG GAT GAG GAT GAA GAT GTT TGC CAA GAA TGT GAT GGT GAT GAA TAC          239
Pro Asp Glu Asp Glu Asp Val Cys Gln Glu Cys Asp Gly Asp Glu Tyr
50                  55                  60                      65

AAA CCA GTT TGC GGA TCT GAC GAC ATA ACT TAC GAT AAC AAC TGT CGA          287
Lys Pro Val Cys Gly Ser Asp Asp Ile Thr Tyr Asp Asn Asn Cys Arg
                70                  75                      80

CTA GAG TGT GCC TCT ATC TCT TCC AGC CCA GGA GTT GAA CTG AAA CAT          335
Leu Glu Cys Ala Ser Ile Ser Ser Ser Pro Gly Val Glu Leu Lys His
            85                  90                  95

GAA GGA CCT TGT AGA ACC GAG GAA AAG AAA ATT CTT AAA AGA TCT GAT          383
Glu Gly Pro Cys Arg Thr Glu Glu Lys Lys Ile Leu Lys Arg Ser Asp
        100                 105                 110

GAA TTC GAA ATG TAT AGA TGC GCA TGT CCG AAA ATA TAT TAT CCG GTT          431
Glu Phe Glu Met Tyr Arg Cys Ala Cys Pro Lys Ile Tyr Tyr Pro Val
    115                 120                 125

TGC GGA ACA GAT GGT GAA ACC TAT CCC AAC TTG TGC GTC CTC GAA TGT          479
Cys Gly Thr Asp Gly Glu Thr Tyr Pro Asn Leu Cys Val Leu Glu Cys
130                 135                 140                 145

CAT ATG AGA ATG AAT CCA GGA CTT CAA TTG CAC CAT TAT GGA CAT TGT          527
His Met Arg Met Asn Pro Gly Leu Gln Leu His His Tyr Gly His Cys
            150                 155                 160

CAA CAT CAT CAT CAC CAT CAT CCT CCT CCT CAT CAC CAT CAT CAT CAT          575
Gln His His His His His His Pro Pro Pro His His His His His His
            165                 170                 175

CAT CCT CAT CAC ACC ACT GAG AAA CCA GTA GAA CCA TGC GCA TGT CCA          623
His Pro His His Thr Thr Glu Lys Pro Val Glu Pro Cys Ala Cys Pro
        180                 185                 190

CAT GCT CTG CAT AGA GTT TGC GGC TCT GAT GGT GAA ACT TAT AGC AAC          671
His Ala Leu His Arg Val Cys Gly Ser Asp Gly Glu Thr Tyr Ser Asn
    195                 200                 205

CCT TGT ACG CTG AAC TGT GCT AAA CAC AAT GGA AAG CCA GGT CTT GTA          719
Pro Cys Thr Leu Asn Cys Ala Lys His Asn Gly Lys Pro Gly Leu Val
```

| | | | | | | | | | | | | | | | |
|---|---|---|---|---|---|---|---|---|---|---|---|---|---|---|---|
|210| | | | |215| | | | |220| | | | |225|

```
AAA  GTC  CAT  GAT  GGT  CCT  TGC  GAA  CCG  GAT  GAG  GAT  GAA  GAT  GTT  TGC       767
Lys  Val  His  Asp  Gly  Pro  Cys  Glu  Pro  Asp  Glu  Asp  Glu  Asp  Val  Cys
               230                           235                      240

CAA  GAA  TGT  GAT  GAT  GTC  GAT  TAC  GAA  CCA  GTT  TGT  GGA  ACT  GAC  GAC       815
Gln  Glu  Cys  Asp  Asp  Val  Asp  Tyr  Glu  Pro  Val  Cys  Gly  Thr  Asp  Asp
               245                           250                      255

AAA  ACT  TAC  GAT  AAC  AAC  TGT  CGA  CTA  GAG  TGT  GCC  TCT  ATC  TCT  TCC       863
Lys  Thr  Tyr  Asp  Asn  Asn  Cys  Arg  Leu  Glu  Cys  Ala  Ser  Ile  Ser  Ser
               260                           265                      270

AGC  CCA  GGA  GTT  GAA  CTG  AAA  CAT  GAA  GGG  ATA  TGT  AGA  AAG  GAG  GAA       911
Ser  Pro  Gly  Val  Glu  Leu  Lys  His  Glu  Gly  Ile  Cys  Arg  Lys  Glu  Glu
     275                      280                      285

AAG  AAA  CTT  CCT  AAA  AGA  TCT  GTG  GGA  TTG  GAA  CAT  ACA  TGC  GTC  TGT       959
Lys  Lys  Leu  Pro  Lys  Arg  Ser  Val  Gly  Leu  Glu  His  Thr  Cys  Val  Cys
290                 295                      300                      305

CCT  TAT  AAT  TAT  TTC  CCG  GTT  TGC  GGA  ACA  GAT  GGG  GAA  ACC  TAT  CCC      1007
Pro  Tyr  Asn  Tyr  Phe  Pro  Val  Cys  Gly  Thr  Asp  Gly  Glu  Thr  Tyr  Pro
                    310                      315                      320

AAC  TTG  TGC  GCC  CTC  CAA  TGC  CGT  ATG  AGA  GAA  GTT  CCA  GGA  CTT  GAA      1055
Asn  Leu  Cys  Ala  Leu  Gln  Cys  Arg  Met  Arg  Glu  Val  Pro  Gly  Leu  Glu
               325                           330                      335

CTG  AAG  CAC  ACA  GGA  AAA  TGT  CTA  CCC  CAT  TTG  GAT  TTT  CCC  GAC  CCA      1103
Leu  Lys  His  Thr  Gly  Lys  Cys  Leu  Pro  His  Leu  Asp  Phe  Pro  Asp  Pro
               340                           345                      350

GTT                                                                                  1156
Val       TAAAGCTTGC  ACATAACGGA  AAATGCACTA  TAGCAGAGTT  ATATCACGGT

TTATTGTAAA  AAAAGATTAT  ATGAATTTAT  CATAATATCA  ATAAAATAGC  TTATTTTAAA              1216

AATATTGAAC  CAATTTAAAT  TTTCAACATA  TGTATATGTA  AATAAATTTA  AAAAAAAAAA              1276

AAAAAA                                                                              1282
```

( 2 ) INFORMATION FOR SEQ ID NO: 17:

( i ) SEQUENCE CHARACTERISTICS:
        ( A ) LENGTH: 368 amino acids
        ( B ) TYPE: amino acid
        ( D ) TOPOLOGY: linear ( x i ) SEQUENCE DESCRIPTION: SEQ ID NO: 17:

```
Arg  Leu  Leu  Leu  Leu  Leu  Gly  Leu  Ala  Ala  Leu  Val  Ala  Ala  Glu  Gly
-14            -10                      -5                            1

Gly  Glu  Pro  Cys  Ala  Cys  Pro  His  Ala  Leu  His  Arg  Val  Cys  Gly  Ser
          5                   10                      15

Asp  Gly  Glu  Thr  Tyr  Ser  Asn  Pro  Cys  Thr  Leu  Asn  Cys  Ala  Lys  Phe
     20                   25                      30

Asn  Gly  Lys  Pro  Glu  Leu  Val  Lys  Val  His  Asp  Gly  Pro  Cys  Glu  Pro
35                      40                      45                      50

Asp  Glu  Asp  Glu  Asp  Val  Cys  Gln  Glu  Cys  Asp  Gly  Asp  Glu  Tyr  Lys
                    55                      60                      65

Pro  Val  Cys  Gly  Ser  Asp  Asp  Ile  Thr  Tyr  Asp  Asn  Asn  Cys  Arg  Leu
               70                      75                      80

Glu  Cys  Ala  Ser  Ile  Ser  Ser  Pro  Gly  Val  Glu  Leu  Lys  His  Glu
          85                      90                      95

Gly  Pro  Cys  Arg  Thr  Glu  Glu  Lys  Lys  Ile  Leu  Lys  Arg  Ser  Asp  Glu
     100                      105                     110

Phe  Glu  Met  Tyr  Arg  Cys  Ala  Cys  Pro  Lys  Ile  Tyr  Tyr  Pro  Val  Cys
115                      120                     125                     130
```

```
Gly  Thr  Asp  Gly  Glu  Thr  Tyr  Pro  Asn  Leu  Cys  Val  Leu  Glu  Cys  His
               135                140                          145

Met  Arg  Met  Asn  Pro  Gly  Leu  Gln  Leu  His  His  Tyr  Gly  His  Cys  Gln
               150                155                          160

His  His  His  His  His  His  Pro  Pro  Pro  His  His  His  His  His  His  His
          165                     170                     175

Pro  His  His  Thr  Thr  Glu  Lys  Pro  Val  Glu  Pro  Cys  Ala  Cys  Pro  His
     180                     185                     190

Ala  Leu  His  Arg  Val  Cys  Gly  Ser  Asp  Gly  Glu  Thr  Tyr  Ser  Asn  Pro
195                          200                205                          210

Cys  Thr  Leu  Asn  Cys  Ala  Lys  His  Asn  Gly  Lys  Pro  Gly  Leu  Val  Lys
                    215                     220                          225

Val  His  Asp  Gly  Pro  Cys  Glu  Pro  Asp  Glu  Asp  Glu  Asp  Val  Cys  Gln
               230                     235                     240

Glu  Cys  Asp  Asp  Val  Asp  Tyr  Glu  Pro  Val  Cys  Gly  Thr  Asp  Asp  Lys
          245                     250                     255

Thr  Tyr  Asp  Asn  Asn  Cys  Arg  Leu  Glu  Cys  Ala  Ser  Ile  Ser  Ser  Ser
     260                     265                     270

Pro  Gly  Val  Glu  Leu  Lys  His  Glu  Gly  Ile  Cys  Arg  Lys  Glu  Glu  Lys
275                          280                     285                     290

Lys  Leu  Pro  Lys  Arg  Ser  Val  Gly  Leu  Glu  His  Thr  Cys  Val  Cys  Pro
                    295                     300                     305

Tyr  Asn  Tyr  Phe  Pro  Val  Cys  Gly  Thr  Asp  Gly  Glu  Thr  Tyr  Pro  Asn
               310                     315                     320

Leu  Cys  Ala  Leu  Gln  Cys  Arg  Met  Arg  Glu  Val  Pro  Gly  Leu  Glu  Leu
          325                     330                     335

Lys  His  Thr  Gly  Lys  Cys  Leu  Pro  His  Leu  Asp  Phe  Pro  Asp  Pro  Val
     340                     345                     350
```

( 2 ) INFORMATION FOR SEQ ID NO: 18:

( i ) SEQUENCE CHARACTERISTICS:
        ( A ) LENGTH: 11 amino acids
        ( B ) TYPE: amino acid
        ( D ) TOPOLOGY: linear ( x i ) SEQUENCE DESCRIPTION: SEQ ID NO: 18:

```
Glu  Gly  Gly  Glu  Pro  Cys  Ala  Cys  Pro  His  Ala
 1                    5                        10
```

( 2 ) INFORMATION FOR SEQ ID NO: 19:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 19:

GAAGGTGGTG AACCNTGYGC NTGYCCNCAY GC  32

( 2 ) INFORMATION FOR SEQ ID NO: 20:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 20:

CGAGGGGGAT GGTCGACGGA AGCGACCTTT TTTTTTTTTT TTTTT  45

(2) INFORMATION FOR SEQ ID NO: 21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 21:

CGAGGGGGAT GGTCGACGG          19

(2) INFORMATION FOR SEQ ID NO: 22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 22:

GATGGTCGAC GGAAGCGACC          20